United States Patent
Tsuchida et al.

(10) Patent No.: US 7,754,879 B2
(45) Date of Patent: Jul. 13, 2010

(54) PORPHYRIN COMPOUND, ALBUMIN INCLUSION COMPOUND THEREOF AND ARTIFICIAL OXYGEN CARRIER

(75) Inventors: Eishun Tsuchida, Tokyo (JP); Teruyuki Komatsu, Tachikawa (JP); Akito Nakagawa, Tokyo (JP); Naomi Ohmichi, Tokyo (JP)

(73) Assignee: Nipro Corporation, Osaka (JP)

( * ) Notice: Subject to any disclaimer, the term of this patent is extended or adjusted under 35 U.S.C. 154(b) by 0 days.

(21) Appl. No.: 12/381,604

(22) Filed: Mar. 13, 2009

(65) Prior Publication Data

US 2009/0182125 A1 Jul. 16, 2009

Related U.S. Application Data

(63) Continuation of application No. 11/199,726, filed on Aug. 9, 2005, now Pat. No. 7,595,394, which is a continuation of application No. 10/799,128, filed on Mar. 12, 2004, now abandoned.

(30) Foreign Application Priority Data

Mar. 14, 2003 (JP) ............................. 2003-069760

(51) Int. Cl.
C07B 47/00 (2006.01)
(52) U.S. Cl. ..................................... 540/145
(58) Field of Classification Search ............... 540/145; 514/185, 410
See application file for complete search history.

(56) References Cited

FOREIGN PATENT DOCUMENTS

| EP | 0739634 | 10/1996 |
|---|---|---|
| JP | 59162924 | 9/1984 |
| JP | 59164791 | 9/1984 |
| JP | 6271577 | 9/1994 |
| JP | 8301873 | * 11/1996 |
| JP | 2001-131200 | * 5/2001 |

OTHER PUBLICATIONS

Collman, "Synthetic Models for the Oxygen-Binding Hemoproteins," Acc. Chem. Res., vol. 10, 1977, pp. 265-272.
Basolo et al., "Synthetic Oxygen Carriers of Biological Interest," Acc. Chem. Res., vol. 8, 1975, pp. 384-395.
Collman et al., "Picket Fence Porphyrins," Synthetic Models for Oxygen-Binding Hemoproteins, Acc. Chem. Res., vol. 97, 1975, pp. 1427-1439.
Tsuchida et al., "Liposomal Heme as Oxygen Carrier Under Semi-Physiological Conditions," Chem. Soc., Dalton Trans., 1984, pp. 1147-1151.
W.S. Brinigar et al., "Solvent Effects on Reversibel Formation and Oxidative Stability of Heme-Oxygen Complexes," Am. Chem. Soc., vol. 96, 1974, pp. 5596-5599.
European Search Report for corresponding Application No. 04005777 dated Jul. 20, 2004.
Traylor et al., "Syntheses and NMR Characterization of Chelated Heme Models of Hemoproteins," Journal of the Am. Chem. Soc., Washington, D.C., wol. 101, No. 22, Oct. 24, 1979, pp. 6716-6731.
Matthew et al., Biochemistry. Second Edition 1996. The Benjamin/Cummings Publishing Company, Inc., pp. 129-138.
Office Action for corresponding Japanese Patent Application No. 2003-069760 dated Oct. 31, 2006.
Molokoedov, A. S. et al., "Zhurnal Obshchei Khimii," vol. 47, No. 5, 1977, pp. 1165-1172.
Rozhkova et al., "Solution Coordination Chemistry of Protohaemin IX Peptide Derivatives," Journal of Porphyrins and Phtalocyanines, vol. 3, No. 8, 1999, pp. 961-702.
Komatsu et al., "Effect of Heme Structure on $O_2$-Binding properties of Human Serum Albumin-Heme Hybrids: Intramolecular Histidine Coordination Provides a Stable $O_2$-Adduct Complex," Bioconjugate Chem., vol. 13, 2002, pp. 397-402.

* cited by examiner

*Primary Examiner*—James O. Wilson
*Assistant Examiner*—Paul V. Ward
(74) *Attorney, Agent, or Firm*—Ohlandt, Greeley, Ruggiero & Perle, L.L.P.

(57) ABSTRACT

A porphyrin compound represented by general formula (A):

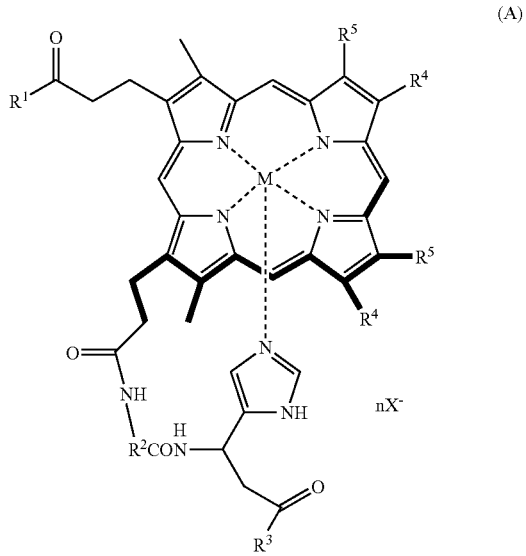

Also disclosed are a porphyrin metal complex-albumin inclusion compound having a porphyrin compound, in which M denotes Fe or Co, included in albumin, and an artificial oxygen carrier containing the porphyrin metal complex-albumin inclusion compound as an active component.

6 Claims, No Drawings

PORPHYRIN COMPOUND, ALBUMIN INCLUSION COMPOUND THEREOF AND ARTIFICIAL OXYGEN CARRIER

CROSS-REFERENCE TO RELATED APPLICATIONS

This present application is a continuation of U.S. application Ser. No. 11/199,726 filed on Aug. 9, 2005 now U.S. Pat. No. 7,595,394, which is a continuation of U.S. application Ser. No. 10/799,128 filed on Mar. 12, 2004 now abandoned, which is based upon and claims the benefit of priority from prior Japanese Patent Application No. 2003-069760, filed Mar. 14, 2003, the entire contents of which are incorporated herein by reference.

BACKGROUND OF THE INVENTION

1. Field of the Invention

The present invention relates to a novel porphyrin compounds such as a porphyrin metal complex, an albumin inclusion compound thereof, and an artificial oxygen carrier.

2. Description of the Related Art

Heme, i.e., a porphyrin iron (II) complex, constituting the active center of hemoglobin or myoglobin that plays the role of carrying and storing oxygen within the living body, is capable of reversibly adsorbing and desorbing molecular oxygen in response to oxygen partial pressure.

Many researches have been reported since 1970's in an effort to achieve the oxygen binding and dissociating capability similar to that performed by natural heme by using a synthetic porphyrin iron (II) complex. As forerunner researches, for example, J. P. Collman, Acc. Chem. Res., 10, 265 (1977) and F. Basolo, B. M. Hoffman, J. A., ibers, Acc. Chem. Res., 8, 384 (1975) can be cited. Particularly, 5,10,15, 20-tetrakis($\alpha,\alpha,\alpha,\alpha$-pivalamidophenylporphyrin iron (II) complex (hereinafter referred to as "FeTpivPP complex") is known as a porphyrin iron (II) complex that is reported to be capable of forming an oxygen complex that is stable under room temperature conditions (see J. P. Collman, et al., J. Am. Chem. Soc., 97, 1427 (1975). The FeTpivPP complex is capable of reversibly adsorbing and desorbing the oxygen molecule at room temperature within an organic solvent such as benzene, toluene, dichloromethane, tetrahydrofuran or N,N-dimethylformamide, if an excess amount of an axial base such as 1-alkylimidazole or 1-alkyl-2-methylimidazole is co-present. Also, if the complex is encapsulated in a bi-layer vesicle made of a phospholipid, the complex similarly exhibits an oxygen binding and dissociating capability even under the physiological conditions (aqueous system, pH 7.4, $\leq 40°$ C.). (see E. Tsuchida et al., J. Chem. Soc., Dalton Trans., 1984, 1147 (1984)).

However, in order to allow the FeTpivPP complex to bind oxygen reversibly, it is necessary to add an excess molar amount of the axial base compound from the outside as pointed out above. Some imidazole derivatives widely used as the axial base may produce a pharmaceutical effect and may exhibit a high toxicity in the living body. Also, in the case of utilizing a phospholipid vesicle, the imidazole derivative that is co-present in an excess amount may make the vesicle unstable. To ultimately decrease the addition amount of the axial base is to introduce the imidazole derivative into the porphyrin molecule by the covalent bond.

The research group including the present inventors have took the position that a stable oxygen carrier can be provided without externally adding the axial base, if an imidazole is covalently bonded, as a side chain substituent, to the porphyrin iron (II) complex. Based on the particular idea, a FeTpivPP analogue having a substituent in the 2-position of the porphyrin ring have been accurately synthesized. Further, an inclusion compound having the FeTpivPP analogue included in the phospholipid vesicle or the human serum albumin has been prepared, providing an artificial oxygen carrier capable of reversibly adsorbing and desorbing oxygen (see Japanese Patent Disclosure (Kokai) No. 59-164791, Japanese Patent Disclosure No. 59-162924, Japanese Patent Disclosure No. 6-271577 and Japanese Patent Disclosure No. 8-301873).

However, most of the synthetic porphyrin iron (II) complexes capable of forming a stable oxygenated complex nowadays are tetraphenylporphyrin iron complexes such as the FeTpivPP analogue. Derivatives having a proximal base covalently bonded to the protoporphyrin iron (II) complex, which constitutes the active center of hemoglobin or myoglobin within the living body, have been synthesized (see W. S. Brinigar, C. K. Chang, J. Geibel, T. G. Traylor, J. Am. Chem. Soc., 96, 5597 (1974)). However, these derivatives tends to readily form a $\mu$-oxo dimer even within an organic solvent such as N,N-dimethylformamide or toluene and, thus, the stability of its oxygenated complex is low, as compared to the tetraphenylporphyrin iron (II) complex. The group of the present inventors have also synthesized a derivative in which an alkylimidazole is covalently bonded to the protoporphyrin iron complex, and prepared an oxygenated complex in respect of the compound having the above-noted derivative included in albumin (see above mentioned Japanese Patent Disclosure No. 8-301873). However, the half-life period of its oxygenated complex is not longer than one hour under 25° C. It follows that the oxygenated complex leaves room for further improvement in terms of the stability in the case of using the oxygenated complex as an artificial oxygen carrier.

Needless to say, the protoporphyrin iron complex derivative is advantageous also in the case where the administration into the living body is taken into account. Protoporphyrin iron (III) that has been no longer utilized in the living body is caught by heme oxidases so as to cleave the $\alpha$-meso position of the porphyrin and thus is decomposed into biliberdin so as to be used in the metabolic process. Since the hydrogen atom in the meso position is substituted with the phenyl ring in the tetraphenylporphyrin iron complex, the tetraphenylporphyrin iron complex may not be decomposed in the metabolic mechanism.

Thus, in the case of considering the use of an aqueous dispersion of a synthetic porphyrin iron (II) complex as an artificial oxygen carrier, e.g., as a substitute for the erythrocyte, development of a molecule design and synthesis of a porphyrin iron derivative capable of forming an oxygenated complex having a higher stability and development of an inclusion compound having the particular porphyrin ion derivative included therein are strongly desired.

BRIEF SUMMARY OF THE INVENTION

An object of the present invention is to provide a porphyrin compound capable of forming an oxygenated complex having a further improved stability, an albumin inclusion compound thereof, and an artificial oxygen carrier.

As described above, the group of the present inventors have synthesized and reported various porphyrin metal complexes having the oxygen binding and dissociating function. Also, the group of the present inventors have provided the porphyrin metal complex-albumin inclusion compound having the porphyrin metal complex included in the serum albumin as an artificial oxygen carrier within water (see Japanese Patent Disclosure No. 8-301873 referred to previously). Further, the group of the present inventors have clarified that, where an intramolecular axially coordinated base is constituted by a histidine derivative, the stability of the oxygenated complex in the porphyrin metal complex-albumin inclusion compound is improved, as compared to the case where the intramolecular axially coordinated base is constituted by an imidazolylalkyl (see T. Komatsu, et al., Bioconjugate Chem., 13, 397 (2002)). The present inventors have continued an extensive research based on the results of the research on the porphyrin metal complex capable of coupling oxygen and the research on the porphyrin metal complex inclusion compound having the porphyrin metal complex included therein as an active site, accomplishing the present invention.

According to the present invention, there is provided a porphyrin compound represented by general formula (A):

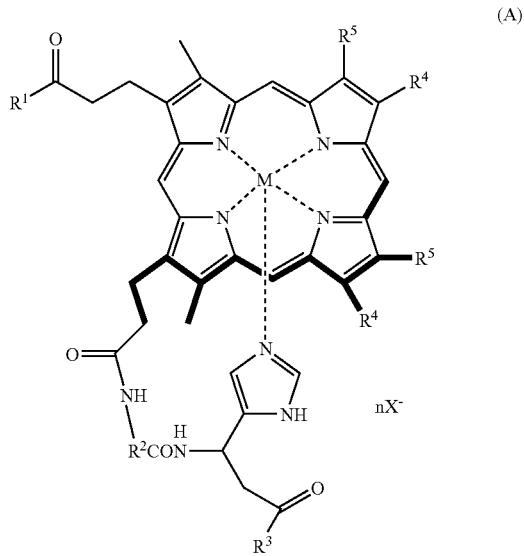

where $R^1$ denotes a $C_1$-$C_{18}$ alkyloxy group, a $C_1$-$C_{18}$ alkylamino group, or a peptide having 1-6 α-amino acids and having a hydroxyl group, a benzyl oxy group or a methoxy group at the C-terminal; $R^2$ denotes a residual group after removal of an amino group and a carboxyl group from an α-amino acid; $R^3$ denotes a $C_1$-$C_{18}$ alkyloxy group, a $C_1$-$C_{18}$ alkylamino group, or a peptide having 1-6 α-amino acids and having a hydroxyl group, a benzyloxy group or a methoxy group at the C-terminal; each $R^4$ and each $R^5$ denote either a methyl group, or a hydrogen atom, a vinyl group, an ethyl group, a 1-methoxyethyl group, a 1-bromoethyl group or a formyl group, wherein, where each $R^4$ denotes a methyl group, each $R^5$ denotes a hydrogen atom, a vinyl group, an ethyl group, a 1-methoxyethyl group, 1-bromoethyl group or a formyl group, and where each $R^4$ denotes a hydrogen atom, a vinyl group, an ethyl group, a 1-methoxyethyl group, a 1-bromoethyl group or a formyl group, each $R^5$ denotes a methyl group; M denotes two hydrogen atoms bonded to the two pyrrole nitrogen atoms or an ion of a transition metal belonging to the fourth to fifth periods in the Periodic Table; $X^-$ denotes a halogen ion that is present where M denotes the transition metal ion; and n which denotes the number of X is the number obtained by subtracting 2 from the valency of the transition metal ion.

Further, where M in general formula (A) denotes Fe or Co, the present invention provides a porphyrin metal complex-albumin inclusion compound having the porphyrin metal complex included in albumin.

Furthermore, the present invention provides an artificial oxygen carrier containing, as an active component, the porphyrin metal complex-albumin inclusion compound of the present invention.

DETAILED DESCRIPTION OF THE INVENTION

The present invention will now be described in detail.
The porphyrin compound of the present invention is represented by general formula (A) given above.

In general formula (A), $R^1$ denotes a $C_1$-$C_{18}$ alkyloxy group, a $C_1$-$C_{18}$ alkylamino group, or a peptide having 1-6 α-amino acids and having a hydroxyl group, a benzyl oxy group or a methoxy group at the C-terminal.

$R^2$ denotes —(R)CH— group in an α-amino acid: $H_2N(R)$CHCOOH (for example, glycine (R=H), alanine (R=—CH$_3$), valine (R=—CH(CH$_3$)$_2$), leucine (R=—CH$_2$CH(CH$_3$)$_2$), and isoleucine (R=—CH(CH$_3$)C$_2$H$_5$), that is, a residual group after removal of an amino group and a carboxyl group from an α-amino acid.

$R^3$ denotes a $C_1$-$C_{18}$ alkyloxy group, a $C_1$-$C_{18}$ alkylamino group, or a peptide having 1-6 α-amino acids and having a hydroxyl group, a benzyloxy group or a methoxy group at the C-terminal.

Each $R^4$ and each $R^5$ denote either a methyl group, or a hydrogen atom, a vinyl group, an ethyl group, a 1-methoxy ethyl group, a 1-bromoethyl group or a formyl group, wherein, where each $R^4$ denotes a methyl group, each $R^5$ denotes a hydrogen atom, a vinyl group, an ethyl group, a 1-methoxyethyl group, 1-bromoethyl group or a formyl group, and where each $R^4$ denotes a hydrogen atom, a vinyl group, an ethyl group, a 1-methoxyethyl group, a 1-bromoethyl group or a formyl group, each $R^5$ denotes a methyl group.

M denotes two hydrogen atoms bonded to two pyrrole nitrogen atoms or an ion of a transition metal belonging to the fourth to fifth periods in the Periodic Table such as chromium, manganese, iron, cobalt or ruthenium. As the transition metal, iron or cobalt is preferred. In the case where the porphyrin compound of the present invention is used as an artificial oxygen carrier adapted for use in the living body, iron is particularly preferred.

$X^-$ denotes a halogen ion that is present in the case where M denotes the transition metal ion, i.e., where the porphyrin compound of the present invention is a metal complex.

Further, n which denotes the number of X is the number obtained by subtracting 2 from the valency of the transition metal ion.

As apparent from the definitions of $R^4$ and $R^5$ given above, the porphyrin compound of the present invention includes the compound represented by formula (A1) given below and the compound represented by formula (A2) given below:

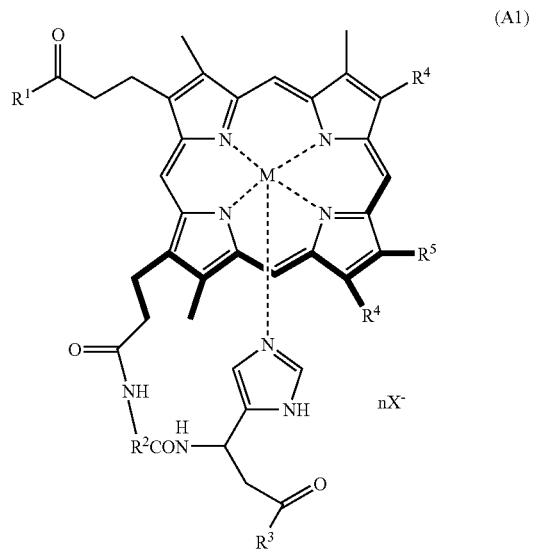

(A1)

where $R^1$-$R^3$, $X^-$, and n are as defined above, and $R^4$ denotes a hydrogen atom, a vinyl group, an ethyl group, a 1-methoxyethyl group, a 1-bromoethyl group or a formyl group.

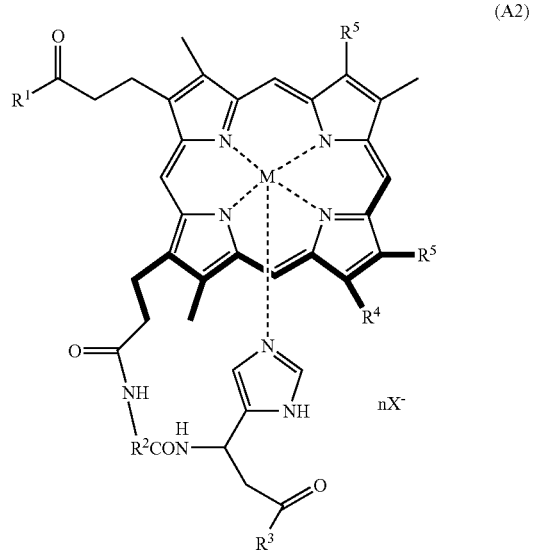

(A2)

where $R^1$-$R^3$, $X^-$, and n are as defined above, and $R^5$ denotes a hydrogen atom, a vinyl group, an ethyl group, a 1-methoxyethyl group, a 1-bromoethyl group or a formyl group.

The porphyrin compound of the present invention can be synthesized by various methods. For example, the compound can be synthesized by reacting a porphyrin represented by formula (1) given below with a histidine derivative represented by formula (2) given below:

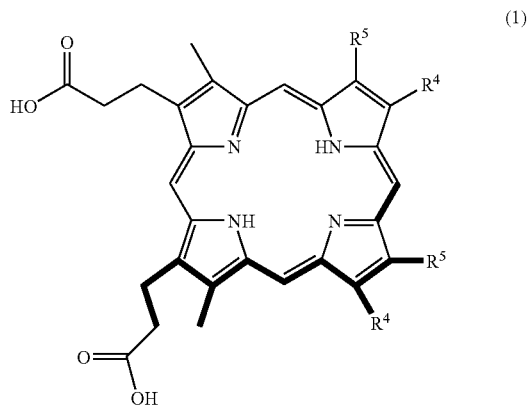

(1)

where $R^4$ and $R^5$ are as defined above;

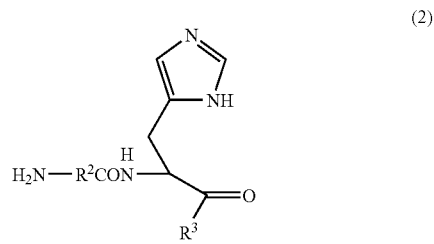

(2)

where $R^2$ and $R^3$ are as defined above.

In carrying out the reaction, the porphyrin represented by formula (1) may be used in the form of, for example, a disodium salt. Also, the histidine derivative represented by formula (2) may be used in the form of a hydrohalide salt. The porphyrin represented by formula (1) includes, for example, protoporphyrin IX, meso-porphyrin IX, and deuteroporphyrin IX.

Also, the histidine derivative represented by formula (2) can be prepared according to an ordinary method by subjecting histidine and the α-amino acid: $H_2N(R)CHCOOH$ noted above to amide forming reaction between the amino group of histidine and the carboxyl group of the α-amino acid, followed by modifying the carboxyl group of histidine. In other words, the histidine derivative can be obtained by the reaction between the histidine after reaction with α-amino acid and an alcohol: $R^0OH$, where $R^0$ denotes a $C_1$-$C_{18}$ alkyl group to esterify the histidine (where $R^3$ denotes a $C_1$-$C_{18}$ alkyl group), or with an amine: $R^0NH_2$, where $R^0$ denotes a $C_1$-$C_{18}$ alkyl group to amidate the histidine (where $R^3$ denotes a $C_1$-$C_{18}$ alkylamino group), according to an ordinary method. Alternatively, where $R^3$ denotes a peptide, the histidine after reaction with the α-amino acid is successively subjected to the reaction with the α-amino acid: $H_2N(R)CHCOOH$ according to an ordinary method, and the C-terminal is converted into a benzyl ester or an amino ester according to an ordinary method, as required. The histidine derivative represented by formula (2) is commercially available.

More specifically, the porphyrin represented by formula (1) is dissolved in a suitable organic solvent such as pyridine or dimethylformamide (DMF), followed by adding an activating agent for activating the carboxyl group of the porphyrin represented by formula (1), for example, (benzotriazole-1-yloxy)tris(dimethylamino)phosphonium hexafluorophosphoric acid (BOP), to the resultant solution, and the mixture thus obtained is stirred for, e.g., 10 minutes to one hour. The activating agent such as BOP can be used in an amount of at least 2 moles relative to one mole of porphyrin represented by formula (1) in the case where the histidine derivative represented by formula (2) is reacted with one of the two carboxyl groups of porphyrin, and the other carboxyl group is modified as described herein later. On the other hand, activating agent such as BOP can be used in an amount of 1.0-2.0 moles relative to one mole of the porphyrin represented by formula (1) in the case where the histidine derivative represented by formula (2) is reacted with one of the two carboxyl groups of the porphyrin and the other carboxyl group is not modified.

Then, the histidine derivative represented by formula (2), which is dissolved in a suitable organic solvent such as DMF or pyridine, is slowly added by using, for example, a dropping funnel to the reaction mixture after the stirring noted above. The histidine derivative can be used in an amount of 0.5 to 1.0 mole relative to one mole of the porphyrin represented by formula (1). After completion of the addition, the reaction mixture is stirred at room temperature for, e.g., 1 to 12 hours under the condition that the light is shielded so as to carry out the desired reaction. A porphyrin compound represented by formula (3) given below can be obtained by this reaction:

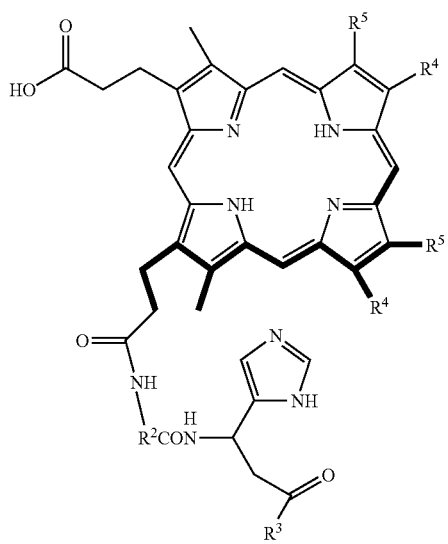

(3)

Then, where the carboxyl group that is not bonded to histidine in formula (3) given above is modified, the porphyrin compound represented by formula (3) is reacted with an alcohol: $R^0OH$, where $R^0$ denotes a $C_1$-$C_{18}$ alkyl group, to esterify the carboxyl group (where $R^1$ is a $C_1$-$C_{18}$ alkyl oxy group), or with an amine: $R^0NH_2$, where $R^0$ denotes a $C_1$-$C_{18}$ alkyl group, to amidate the carboxyl group (where $R^1$ is a $C_1$-$C_{18}$ alkyl amino group). Also, where $R^1$ denotes the peptide, the histidine after the reaction with the α-amino acid is successively reacted with the α-amino acid: $H_2N(R)$CHCOOH so as to convert the C-terminal into a benzyl ester or an amino ester by an ordinary method, as required. As a result, a porphyrin compound represented by formula (4) given below is obtained in which $R^1$ denotes an atomic group other than the hydroxyl group:

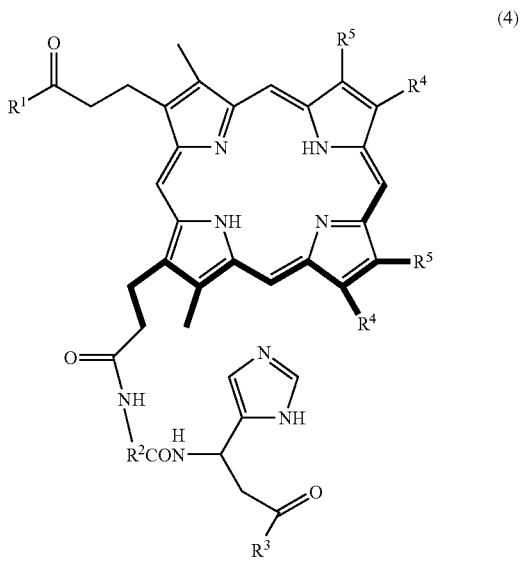

(4)

In order to introduce a transition metal M into the porphyrin compound represented by formula (3) or formula (4), it is possible to employ the general method described in, for example, The Porphyrin, 1978, compiled by D. Dolphin and published by Academic Press Inc. In general, an iron (III) complex is obtained in the case of an iron complex, or a cobalt (II) complex is obtained in the case of a cobalt complex.

Among the porphyrin metal complexes described above, the iron (III) complex can be reduced into the iron (II) complex by using a suitable reducing agent such as sodium dithionite or ascorbic acid according to an ordinary method so as to develop an oxygen binding activity.

As apparent from the definition of formula (1), the porphyrin compound of the present invention comprises a metal free porphyrin compound in which M denotes two hydrogen atoms, and a porphyrin metal complex in which M denotes a transition metal. Where the central metal M is in +2 in the latter metal complex, the imidazole group of the histidine derivative covalently bonded to the propionic acid residue bonded to the porphyrin ring is coordinated with the central metal M as a proximal base. As a result, the porphyrin metal complex of the present invention the +2 central metal M can exhibit an oxygen binding capability by itself so as to make it unnecessary to add from the outside an imidazole derivative as an axial base. Where the porphyrin metal complex comprises iron or cobalt as the central metal M, the porphyrin metal complex can be encapsulated in a phospholipid bi-layer vesicle by an ordinary method (see Japanese Patent Disclosure No. 8-301873 referred to previously), or can be enclosed in a phospholipid-encapsulated fat emulsion (see Japanese Patent Disclosure No. 6-184156). The porphyrin metal complex can also be included in albumins such as a bovine serum albumin, a human serum albumin, a recombinant human serum albumin, and a polymer albumin (see T. Komatsu, et al., Bioconjugate Chem., 13, 387 (2002)). Among the system thus obtained, the porphyrin iron or cobalt complex of the present invention is capable of promptly forming a stable oxygenated complex upon contact with oxygen even in an aqueous system. Also, the porphyrin metal complex of the present invention is capable of adsorbing and desorbing oxygen in accordance with the oxygen partial pressure. The binding and dissociating of oxygen can be reversibly effected repeatedly. It should be noted that, in the porphyrin metal complex of the present invention, a derivative of histidine, which is one of the natural amino acids, is used as a proximal base, and a porphyrin having the meso-position not modified is used as the porphyrin. It follows that the porphyrin metal complex of the present invention can provide a useful artificial oxygen carrier that is highly excellent in the adaptability to the living body.

It is expected for the porphyrin metal complex of the present invention to be utilized as an artificial oxygen carrier in, for example, a substitute for a transfusing blood, a blood diluent before the surgical operation, a replenishing solution in an external circulating circuit such as an artificial lung, a perfusion solution of a transplanted internal organs, an oxygen supply solution into the ischemia portion, a treating agent of a chronic amenia, a perfusion solution for a liquid ventilation, a sensitizing agent for curing cancer, and a culture solution for a regenerated tissue cell. It is also expected for the porphyrin metal complex of the present invention to be utilized in a rare blood type patient, a patient who denies blood transfusion for religious reasons, and an animal therapy.

In addition, where the porphyrin compound of the present invention is in the form of a complex of an ion of a metal belonging to, for example, the fourth period of the Periodic Table, the complex can be utilized as a catalyst in an oxygen reducing reaction, an oxygen oxidizing reaction or an oxygen addition reaction. In other words, the porphyrin metal complex of the present invention can be used as, particularly, an adsorbing-desorbing agent of an oxygen gas, as a redox catalyst, as a catalyst for an oxygen oxidizing reaction, and as a catalyst for an oxygen addition reaction in addition to the use as an artificial oxygen carrier.

In addition to oxygen, a gas capable of coordination with the central metal M, such as carbon monoxide, nitrogen monoxide or nitrogen dioxide can form a coordinated complex with the porphyrin metal complex of the present invention. It follows that the porphyrin metal complex of the present invention can be used as an adsorbent of such a gas.

The present invention will now be described with reference to Examples which follow. However, the present invention should not be limited to the following Examples.

Example 1

Protoporphyrin IX (400 mg (0.71 mmol)) was dissolved in pyridine (40 mL), and the resultant solution was stirred at room temperature for 10 minutes. Then, BOP (840 mg (1.9 mmol)) was added to the solution, and the solution was further stirred for 10 minutes. Further, a solution of glycyl-L-histidine methyl ester dihydrochloride (129 mg (0.57 mmol)) in DMF (15 mL) was slowly added dropwise into the resultant solution by using a dropping funnel. The reaction mixture was stirred for 2.5 hours at room temperature under a light-shielded condition, followed by adding ethanol (4.2 mL (71 mmol)) to the reaction mixture, and the mixture was stirred for 18 hours. The resultant reaction solution (15 to 20 mL) was added dropwise into ice water (1 L) and, then, centrifugally separated (7,000 g, 30 minutes), followed by filtering the precipitated material with a G4 glass filter and subsequently dissolving the filtrate in a chloroform/methanol mixed solvent. After the solvent was removed under a reduced pressure, the residue was fractionated with a silica gel column (chloroform/methanol=10/1 (v/v). After the solvent was removed under a reduced pressure from the obtained fraction, the residue was further fractionated with a silica gel column (silica gel-60, chloroform/methanol=15/1 (v/v)). The fraction thus obtained was dried under vacuum to give 100 mg of the desired porphyrin compound: 3,8-divinyl-2,7,12,18-tetramethyl-13-(2-((N-glycyl-(O-methyl)histidine)carbamoyl)ethyl)-17-((ethoxycarbonyl)ethyl)porphyrin (yield of 20%).

<Analytical Result>

Thin layer chromatography (MERCK silica gel plate, chloroform/methanol=10/1 (v/v); Rf: 0.42 (monospot)

FAB mass spectrum: 785 [M-H$^+$]

Infrared ray absorption spectrum (cm$^{-1}$): 1635 ($v_{C=O}$ (amide)); 1725 ($v_{C=O}$ (ester))

Visible light absorption spectrum (chloroform): $\lambda_{max}$: 625; 577; 541; 505; 405 nm $^1$H-NMR (d-DMSO, TMS standard); δ(ppm): −4.6 (s, 2H, inner-NH; 2.7-2.9 (m, 2H, Im-CH$_2$—); 3.0-3.5 (m, 18H, por-CH$_3$, —CH$_2$—CH$_2$—CO—NH—, —CH$_2$—CH$_2$—COO—CH$_2$—CH$_3$); 3.6 (s, 2H, —CONH—CH$_2$—CONH—); 3.8 (s, 3H, —OCH$_3$); 4.0-4.3 (d, 4H, por-CH$_2$—); 4.3-4.5 (m, 1H, α-CH); 6.0-6.4 (m, 4H, vinyl=CH$_2$); 7.4 (s, 1H, imidazole ring H); 8.0-8.3 (m, 5H, vinyl-CH, imidazole ring H); 9.8-10 (m, 4H, meso position-H). "Im" given above indicates imidazole, and "por" indicates porphyrin; the same applies below.

Example 2

The porphyrin compound obtained in Example 1 (50 mg (64 μmol)) was added to a mixed solution of anhydrous DMF (20 mL) and 2,6-lutidine (37.1 μL (1.13 mmol)), and the result solution was deaerated with argon for 20 minutes. Then, ferric chloride tetrahydrate (89 mg (1.13 mmol)) was added to the resultant solution at 60° C. and the mixture was stirred for 4 hours under an argon gas atmosphere. The resultant reaction solution was added dropwise into ice water (1 L), followed by adding potassium iodide (5 g), and subsequently subjecting to a centrifugal separation (5000 g, 20 minutes). Then, the precipitated material was filtered with a G4 glass filter, followed by dissolving the filtrate in a chloroform/methanol mixed solvent. After the solvent was removed under a reduced pressure, the residue was fractionated with a silica gel column (chloroform/methanol=5/1 (v/v)). The fraction thus obtained was dried under vacuum to give 33.3 mg of the desired porphyrin iron complex: [3,8-divinyl-2,7,12,18-tetramethyl-13-(2-((N-glycyl-(O-methyl)histidine)carbamoyl) ethyl]-17-((ethoxycarbonyl)ethyl)porphyrinato]iron (III) iodide (yield of 62%).

<Analytical Result>

Thin layer chromatography (MERCK silica gel plate, chloroform/methanol=10/1 (v/v); Rf: 0.5 (monospot)

FAB mass spectrum: 838 [M-I$^-$]

Infrared ray absorption spectrum (cm$^{-1}$): 1660 ($v_{C=O}$ (amide)); 1734 ($v_{C=O}$ (ester))

Visible light absorption spectrum (chloroform): $\lambda_{max}$: 637; 508; 388 nm Example 3

Meso-porphyrin IX (500 mg (0.78 mmol)) was dissolved in pyridine (40 mL), and the resultant solution was stirred at room temperature for 10 minutes. Then, BOP (930 mg (2.1 mmol)) was added to the resultant solution, followed by further stirring the solution for 10 minutes. After a solution of alanyl-L-histidine decyl ester dihydrochloride (221 mg (0.63 mmol)) in pyridine (15 mL) was slowly added dropwise into the resultant solution by using a dropping funnel, the solution was stirred at room temperature for 6 hours under a light-shielded condition. After the solvent was removed under a reduced pressure, the residue was extracted with chloroform, and washed twice with hydrochloric acid (pH 5) and twice with water, followed by drying the extracted material over anhydrous sodium sulfate. The extracted material was filtered, and the solvent was removed under a reduced pressure. Further, the residue was fractionated with a silica gel column (chloroform/methanol=20/1 (v/v)). The fraction thus obtained was dried under vacuum to give 146 mg of the desired porphyrin compound: 3,8-diethyl-2,7,12,18-tetramethyl-13-(2-((N-alanyl-L-(O-decyl)histidine)carbamoyl) ethyl)-17-(carboxyethyl)porphyrin hydrochloride (yield of 20%).

<Analytical Result>

Thin layer chromatography (MERCK silica gel plate, chloroform/methanol=20/1 (v/v); Rf: 0.4 (monospot)

FAB mass spectrum: 939.5 [M-H$^+$]

Infrared ray absorption spectrum (cm$^{-1}$): 1635 ($\nu_{C=O}$ (amide)); 1705 ($\nu_{C=O}$ (carboxylic acid))

Visible light absorption spectrum (chloroform): $\lambda_{max}$: 626; 576; 540; 504; 404 nm $^1$H-NMR (CDCl$_3$, TMS standard); δ(ppm): −4.6 (s, 2H, inner-NH; 0.96 (t, 3H, —CH$_2$CH$_2$CH$_3$); 1.3-1.6 (m, 19H, —CH(CH$_3$)—, —OCH$_2$(CH$_2$)$_8$CH$_3$); 2.0 (m, 6H, por-CH$_2$CH$_3$): 2.7-2.9 (m, 2H, Im-CH$_2$—); 3.0-3.5 (m, 18H, por-CH$_3$, CH$_2$—CH$_2$—CO—NH, —CH$_2$—CH$_2$—COOH); 4.0 (m, 2H, —C(=O)O—CH$_2$—); 4.1-4.3 (m, 4H, por-CH$_2$—CH$_2$—); 4.4 (d, 4H, por-CH$_2$—CH$_3$); 4.6-4.7 (m, 2H, α-CH); 7.4 (s, 1H, imidazole ring H); 8.0 (m, 1H, imidazole ring H); 9.8-10 (m, 4H, meso position-H).

Example 4

The porphyrin compound obtained in Example 3 (50 mg (53 μmol)) was added to a mixed solution of anhydrous DMF (20 mL) and 2,6-lutidine (31 μL (0.93 mmol)), and an argon gas was passed through the resultant solution for 20 minutes. Further, ferric chloride tetrahydrate (73 mg (0.93 mmol)) was added to the solution, followed by stirring the resultant mixture at 60° C. for 4 hours under an argon gas atmosphere. After the solvent was removed under a reduced pressure, the residue was extracted with chloroform, followed by washing the extract several times with pure water and subsequently drying the extract over anhydrous sodium sulfate. The extract was filtered. After the solvent was removed under a reduced pressure, the residue was fractionated with a silica gel column (chloroform/methanol=20/1 (v/v). The fraction thus obtained was dried under vacuum to give 30 mg of the desired porphyrin iron complex: [3,8-diethyl-2,7,12,18-tetramethyl-13-(2-((N-alanyl-L-(O-decyl)histidine)carbamoyl)ethyl)-17-(carboxyethyl)porphyrinato]iron (III) chloride (yield of 60%).

<Analytical Result>

Thin layer chromatography (MERCK silica gel plate, chloroform/methanol=20/1 (v/v); Rf: 0.37 (monospot)

FAB mass spectrum: 958 [M-Cl$^-$]

Infrared ray absorption spectrum (cm$^{-1}$): 1635 ($\nu_{C=O}$ (amide)); 1705 ($\nu_{C=O}$ (carboxylic acid))

Visible light absorption spectrum (chloroform): $\lambda_{max}$: 636; 507; 387 nm Example 5

Deuteroporphyrin IX dihydrochloride (400 mg (0.69 mmol)) was dissolved in pyridine (50 mL), and the resultant solution was stirred at room temperature for 10 minutes. Then, BOP (816 mg (1.8 mmol)) was added to the resultant solution, followed by further stirring the solution for 10 minutes. After a solution of valyl-L-histidinyl leucyl-leucine methyl ester dihydrochloride (3741 mg (0.55 mmol)) in pyridine (15 mL) was slowly added dropwise into the resultant solution by using a dropping funnel, the solution was stirred at room temperature for 6 hours under a light-shielded condition. Further, hexylamine (9.1 mL (69 mmol)) was added dropwise to the solution, followed by further stirring the solution for 15 hours. After the solvent was removed from the reaction mixture under a reduced pressure, the residue was extracted with chloroform, and washed with water, followed by drying the extracted material over anhydrous sodium sulfate. The extracted material was filtered, and the solvent was removed under a reduced pressure. The residue was fractionated with a silica gel column (chloroform/diethyl ether=20/1 (v/v)). The fraction thus obtained was dried under vacuum to give 130 mg of the desired porphyrin compound: 2,7,12,18-tetramethyl-13-(2-(hexyl carbamoyl)ethyl)-17-(2-((N-valyl-L-histidyl-leucyl-leucyl-(O-methyl)leucine)carbamoyl) ethyl)porphyrin (yield of 15%).

<Analytical Result>

Thin layer chromatography (MERCK silica gel plate, chloroform/diethyl ether=20/1 (v/v); Rf: 0.4 (monospot)

FAB mass spectrum: 1257 [M-H$^+$]

Infrared ray absorption spectrum (cm$^{-1}$): 1635 ($\nu_{C=O}$ (amide)))

Visible light absorption spectrum (chloroform): $\lambda_{max}$: 627; 577; 541; 505; 405 nm $^1$H-NMR (CDCl$_3$, TMS standard); δ(ppm): −4.6 (s, 2H, inner-NH; 1.0 (m, 27H, —CHCH$_3$)CH$_3$, —NH(CH$_2$)$_9$CH$_3$); 1.3-1.5 (16H, m, —NH(CH$_2$)(CH$_2$)$_8$CH$_3$); 1.7-2.2 (m, 10H, —CH(CH$_3$)CH$_3$, —CH$_2$CH(CH$_3$)CH$_3$; 2.7-2.9 (m, 2H, Im-CH$_2$—); 3.0-3.5 (m, 18H, por-CH$_3$, —CH$_2$—CH$_2$—CO—NH—, —NH—CH$_2$(CH$_2$)$_8$CH$_3$; 3.7 (s, 3H, —OCH$_3$); 4.1-4.3 (m, 4H, por, —CH$_2$—); 4.3-4.5 (m, 5H, α-CH); 7.4 (s, 1H, imidazole ring H); 8.0 (m, 1H, imidazole ring H); 9.8-10 (m, 6H, por-H).

Example 6

The porphyrin compound obtained in Example 5 (100 mg (80 μmol)) was added to a mixed solution of anhydrous DMF (30 mL) and 2,6-lutidine (46 μL (1.40 mmol)), and the resultant solution was stirred by passing an argon gas into the solution. Further, ferric chloride tetrahydrate (109 mg (1.40 mmol)) was added to the solution, followed by stirring the resultant mixture at 60° C. for 5 hours under an argon gas atmosphere. After the solvent was removed under a reduced pressure, the residue was extracted with chloroform, followed by washing the extract several times with purified water and subsequently drying the extract over anhydrous sodium sulfate. The extract was filtered. After the solvent was removed under a reduced pressure, the residue was fractionated with a silica gel column (chloroform/diethyl ether=20/1 (v/v)). The fraction thus obtained was dried under vacuum to give 64 mg of the desired porphyrin iron complex: [2,7,12,18-tetramethyl-13-(2-(hexylcarbamoyl)ethyl)-17-(2-((N-valyl-L-histidyl-leucyl-leucyl-(O-methyl)leucine)carbamoyl)porphyrinato]iron (III) chloride (yield of 60%).

<Analytical Result>

Thin layer chromatography (MERCK silica gel plate, chloroform/diethyl ether=20/1 (v/v); Rf: 0.38 (monospot)

FAB mass spectrum: 1312 [M-Cl$^-$]

Infrared ray absorption spectrum (cm$^{-1}$): 1660 ($v_{C=O}$ (amide))

Visible light absorption spectrum (chloroform): $\lambda_{max}$: 637; 508; 388 nm Example 7

After nitrogen substitution, 30 μm DMF solution (3 mL) of the porphyrin iron complex obtained in Example 2 was mixed with a methanol solution of sodium dithionite-18-crown-6-ether complex, and the mixture was stirred for 10 minutes so as to reduce the central iron of the porphyrin iron complex into the divalent state. As a result, a DMF solution of [3,8-divinyl-2,7,12,18-tetramethyl-13-(2-(N-glycyl-(O-methyl)histidine)carbamoyl)ethyl]-17-((ethoxycarbonyl)ethyl)porphyrinato]iron (II) iodide was obtained. The visible light absorption spectrum of the solution showed $\lambda_{max}$ at 442; 545; and 565 nm, supporting that the porphyrin iron complex corresponds to the 5-coordinated deoxy type in which one imidazole molecule is coordinated with the central iron.

Example 8

The [3,8-divinyl-2,7,12,18-tetramethyl-13-(2-(N-glycyl-(O-methyl)histidine)carbamoyl)ethyl]-17-((ethoxycarbonyl)ethyl)porphyrinato]iron (II) iodide obtained in Example 7 was included into the human serum albumin in accordance with the method disclosed in Japanese Patent Disclosure No. 8-301873, preparing a porphyrin iron complex. Then, a dispersion of the porphyrin iron complex-albumin inclusion compound in a phosphate buffer (porphyrin iron (II) complex: 20 μm; serum albumin: 20 μm) was put in a cell made of quartz for a spectral measurement, and the cell was hermetically sealed under a nitrogen gas atmosphere. The visible light absorption spectrum of the dispersion showed $\lambda_{max}$ at 423; 539; and 569 nm, supporting that the included porphyrin iron (II) complex forms an Fe(II) high spin 5-coordinated complex having a single intramolecular axial base coordinated therein. When oxygen was introduced into the dispersion, $\lambda_{max}$ of the visible light absorption spectrum was changed to 421; 542; and 561 nm, clearly supporting that an oxygenated complex was formed. When a nitrogen gas was blown into the dispersion of the oxygenated complex, the visible light absorption spectrum was reversibly changed from the oxygenation type spectrum into the deoxy-type spectrum, supporting that the adsorption-desorption of oxygen is reversibly brought about. Incidentally, it was possible to perform consecutively the adsorption-desorption of oxygen by alternately repeating the oxygen blow and the nitrogen blow. Also, the half-life period of the oxygenated complex was 90 to 120 minutes at 25° C., and thus is clearly more stable than the oxygen complex of the porphyrin iron complex-albumin inclusion compound reported in the prior art.

As described above, the present invention provides a porphyrin compound capable of forming an oxygenated complex having a further improved stability. The albumin inclusion body of the porphyrin compound can function as an artificial oxygen carrier.

What is claimed is:

1. A metal complex-albumin inclusion compound comprising:
    an albumin; and
    a compound represented by formula (A):

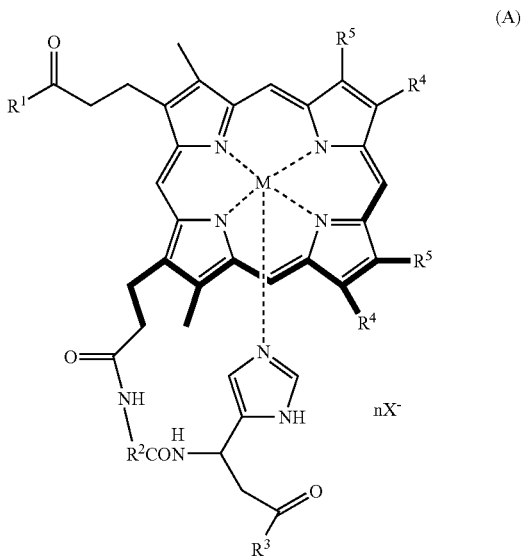

where $R^1$ denotes a $C_1$-$C_{18}$ alkyloxy group, a $C_1$-$C_{18}$ alkylamino group; $R^2$ denotes a residual group after removal of an amino group and a carboxyl group from an α-amino acid selected from the group consisting of glycine, alanine, valine, leucine and isoleucine; $R^3$ denotes a $C_1$-$C_{18}$ alkyloxy group, a $C_1$-$C_{18}$ alkylamino group, or a peptide having 2-6 α-amino acids selected from the group consisting of glycine, alanine, valine, leucine and isoleucine and having a methoxy group at the C-terminal; each $R^4$ and each $R^5$ denote either a methyl group, or a hydrogen atom, a vinyl group, an ethyl group, a 1-methoxyethyl group, a 1-bromoethyl group or a formyl group, wherein, where each $R^4$ denotes a methyl group, each $R^5$ denotes a hydrogen atom, a vinyl group, an ethyl group, a 1-methoxyethyl group, 1-bromoethyl group or a formyl group, and where each $R^4$ denotes a hydrogen atom, a vinyl group, an ethyl group, a 1-methoxyethyl group, a 1-bromoethyl group or a formyl group, each $R^5$ denotes a methyl group; M denotes Fe or Co; $X^-$ denotes a halogen ion; and n which denotes the number of X is the number obtained by subtracting 2 from the valency of the transition metal ion,
    wherein the compound is included in the albumin.

2. The compound according to claim 1, wherein each $R^4$ denotes a hydrogen atom, a vinyl group, an ethyl group, a 1-methoxy ethyl group, a 1-bromo ethyl group or a formyl group, and each $R^5$ denotes a methyl group.

3. The compound according to claim 1, wherein each $R^4$ denotes a methyl group, and each $R^5$ denotes a vinyl group, an ethyl group, a 1-methoxy ethyl group, a 1-bromo ethyl group or a formyl group.

4. The compound according to claim 1, wherein Fe is divalent or trivalent.

5. The compound according to claim 1, wherein Co is divalent.

6. An artificial oxygen carrier comprising the metal complex-albumin inclusion compound defined in claim 1 as an active component.

* * * * *